(12) United States Patent
Suzuki et al.

(10) Patent No.: US 11,419,797 B2
(45) Date of Patent: Aug. 23, 2022

(54) METHOD FOR PRODUCING COMPOSITION CONTAINING HARDLY WATER-SOLUBLE AROMATIC COMPOUND

(71) Applicant: KAO CORPORATION, Tokyo (JP)

(72) Inventors: Takashi Suzuki, Tokyo (JP); Tetsuya Abe, Tokyo (JP); Rui Takahashi, Tokyo (JP); Koji Endo, Tokyo (JP); Toyoki Hagura, Tokyo (JP); Hidetaka Iwai, Tokyo (JP); Teruo Horizumi, Tokyo (JP); Taisuke Aosaki, Tokyo (JP); Akihiro Uda, Tokyo (JP); Masato Nakamichi, Tokyo (JP)

(73) Assignee: KAO CORPORATION, Tokyo (JP)

( * ) Notice: Subject to any disclaimer, the term of this patent is extended or adjusted under 35 U.S.C. 154(b) by 48 days.

(21) Appl. No.: 16/958,331

(22) PCT Filed: Dec. 27, 2018

(86) PCT No.: PCT/JP2018/048376
§ 371 (c)(1),
(2) Date: Jun. 26, 2020

(87) PCT Pub. No.: WO2019/131975
PCT Pub. Date: Jul. 4, 2019

(65) Prior Publication Data
US 2021/0059909 A1   Mar. 4, 2021

(30) Foreign Application Priority Data
Dec. 27, 2017   (JP) .............................. JP2017-251319

(51) Int. Cl.
*A61K 8/04*   (2006.01)
*A61K 8/34*   (2006.01)
(Continued)

(52) U.S. Cl.
CPC ................ *A61K 8/04* (2013.01); *A61K 8/347* (2013.01); *A61K 8/37* (2013.01); *A61Q 19/00* (2013.01);
(Continued)

(58) Field of Classification Search
None
See application file for complete search history.

(56) References Cited

U.S. PATENT DOCUMENTS 6,107,261 A   8/2000 Taylor et al.
6,136,771 A   10/2000 Taylor et al.
(Continued)

FOREIGN PATENT DOCUMENTS

EP   1 057 416 A2   12/2000
EP   3 763 353 A1   1/2021
(Continued)

OTHER PUBLICATIONS

International Search Report (PCT/ISA/210) issued in PCT/JP2018/048376, dated Apr. 2, 2019.
(Continued)

*Primary Examiner* — Kyung S Chang
(74) *Attorney, Agent, or Firm* — Birch, Stewart, Kolasch & Birch, LLP (57) ABSTRACT

Methods for producing a composition containing a hardly water-soluble aromatic compound are described which involve Step (1), including Step (1-1) for preparing a material comprising: (A) a hardly water-soluble aromatic compound, (B) a polyol, and (C) an aqueous medium, where a content of the (A) hardly water-soluble aromatic compound in the material for heating is below a saturation solubility of the (A) hardly water-soluble aromatic compound in a solvent having the same composition at 25° C. The obtained solution is then heated in Step (1-2) at normal pressure at a
(Continued)

temperature of less than 100° C., to obtain a hardly water-soluble aromatic compound solution 1. Step (2) includes adding water to the hardly water-soluble aromatic compound solution 1 such that the resulting hardly water-soluble aromatic compound solution 2 has a concentration of the (A) hardly water-soluble aromatic compound above a saturation solubility at 25° C.

10 Claims, 1 Drawing Sheet

(51) Int. Cl.
 *A61K 8/37* (2006.01)
 *A61Q 19/00* (2006.01)
(52) U.S. Cl.
 CPC ...... *A61K 2800/10* (2013.01); *A61K 2800/49* (2013.01)

(56) References Cited

U.S. PATENT DOCUMENTS

| | | |
|---|---|---|
| 2014/0107048 A1 | 4/2014 | Pan et al. |
| 2014/0107059 A1 | 4/2014 | Pan et al. |
| 2016/0250129 A1 | 9/2016 | Kim et al. |
| 2020/0397675 A1 | 12/2020 | Inoue et al. |

FOREIGN PATENT DOCUMENTS

| | | |
|---|---|---|
| JP | 2003-502353 A | 1/2003 |
| JP | 2005-82506 A | 3/2005 |
| JP | 2008-31126 A | 2/2008 |
| JP | 2011-98919 A | 5/2011 |
| JP | 2014-139164 A | 7/2014 |
| JP | 2015-120656 A | 7/2015 |
| JP | 2015-205873 A | 11/2015 |
| JP | 2015-533170 A | 11/2015 |
| JP | 2016-145180 A | 8/2016 |
| WO | WO 00/78275 A2 | 12/2000 |
| WO | WO 2014/059228 A1 | 4/2014 |
| WO | WO 2019/171529 A1 | 9/2019 |

OTHER PUBLICATIONS

Takehara et al., "New soluhilizing technology at isopropyl methylphenol and its application to cosmetics," The Society of Cosmetic Chemists of Japan, Nov. 29, 2016, pp. 14-15.
Extended European Search Report for European Application No. 18895719.5, dated Feb. 5, 2021.
European Patent Office Communication and extended search report issued in the European Patent Application No. 22162427.3 dated Jun. 27, 2022.

METHOD FOR PRODUCING COMPOSITION CONTAINING HARDLY WATER-SOLUBLE AROMATIC COMPOUND

FIELD OF THE INVENTION

The present invention relates to a method for producing a composition containing a hardly water-soluble aromatic compound.

BACKGROUND OF THE INVENTION

Aromatic compounds are widely used in products such as cosmetics, pharmaceuticals, foods, and daily necessaries. Many aromatic compounds are in a solid state at room temperature and hardly soluble in water, and they are generally used in a dissolved state in alcohols, but skin irritation derived from the alcohols can impair the impression from use. In addition, to use the aromatic compounds with alcohols can limit the composition to be applied.

Accordingly, technologies for solubilizing hardly water-soluble antimicrobial substances in water have been investigated. For example, isopropyl methylphenol glycosides in which sugars such as glucose are linked to isopropyl methylphenol (Patent Literature 1) and a method for solubilizing isopropyl methylphenol in combination with a surfactant and a wetting agent (Patent Literature 2) have been reported. It has been also reported that a method for solubilizing phenolic antimicrobial agents, such as isopropyl methylphenol, by heating together with polyols at 110-180° C. in the presence of an aqueous medium (Patent Literature 3). Patent Literature 3 establishes that heating at a temperature below 100° C. fails to maintain the solubility of isopropyl methylphenol at room temperature after it is cooled.
(Patent Literature 1) JP-A-2005-82506
(Patent Literature 2) JP-A-2011-96919
(Patent Literature 3) JP-A-2014-139164

SUMMARY OF THE INVENTION

The present invention provides a method for producing a composition containing a hardly water-soluble aromatic compound, the method including
Step (1) of obtaining a hardly water-soluble aromatic compound solution 1, Step (1) comprising Step (1-1) of preparing a material for heating, containing (A) a hardly water-soluble aromatic compound, (B) polyols and (C) an aqueous medium, and Step (1-2) of obtaining a heated solution containing a hardly water-soluble aromatic compound by heating the material for heating at normal pressure at a temperature of less than 100° C., and
Step (2) of adding water to the hardly water-soluble aromatic compound solution 1 to obtain a hardly water-soluble aromatic compound solution 2 in which the hardly water-soluble aromatic compound has a concentration above the saturation solubility at 25° C. In Step (1), the content of a surfactant in the material for heating is 0.1 mass % or less, and the content of (A) a hardly water-soluble aromatic compound in the material for heating is (A) below the saturation solubility of the hardly water-soluble aromatic compound in a solvent of the same composition at 25° C.

The present invention further provides a method for producing a solution containing a hardly water-soluble aromatic compound 1, the method including
Step (1-1) of preparing a material for heating containing (A) a hardly water-soluble aromatic compound, (E) a polyol and (C) an aqueous medium, and
Step (1-2) of obtaining a heated solution containing a hardly water-soluble aromatic compound by heating the material for heating at normal pressure at a temperature of less than 100° C.
wherein, in Step (1-2), the material for heating is heated in such a way that the (A) hardly water-soluble aromatic compound is prevented from deposition in a hardly water-soluble aromatic compound solution 2 that is obtained by diluting the hardly water-soluble aromatic compound solution 1 with water such that a concentration of the (A) hardly water-soluble aromatic compound is above a saturation solubility.

DETAILED DESCRIPTION OF THE INVENTION

However, a so-called glycoside in which a sugar is bound to a hardly water-soluble aromatic compound itself such as an isopropyl methylphenol has high solubility in water, but the manufacturing process thereof is complicated, leading to high cost. Therefore, it is not economically preferable to use isopropyl methylphenol glycosides instead of isopropyl methylphenol. In addition, some methods of solubilizing a hardly water-soluble aromatic compound using a surfactant may not give sufficient solubility and effects of the aromatic compound. In contrast, the method of heating at 100 to 180° C. in the presence of an aqueous medium is a technique related to the promotion of solubilization of hardly water-soluble aromatic compounds. However, this method has room for improvement for saving cost etc., because this method requires installing pressure-resistant equipment in the industrial production and necessity of modification in application to heat denaturing, volatile or sublimable substances.

The present invention therefore seeks to provide a new method for producing a composition comprising a hardly water-soluble aromatic compound with excellent solubility of the hardly water-soluble aromatic compound. The present inventors investigated various technologies for solubilizing hardly water-soluble aromatic compounds. As a result, the present inventors found that a composition containing a hardly water-soluble aromatic compound, wherein
even if the material containing a hardly water-soluble aromatic compound, a polyol, and an aqueous medium is heated at normal pressure at a temperature of less than 100° C., the constitution of the material to be heated falls within a specific range, and
even if diluted with water, when a sufficient thermal history is given, deposition of the hardly water-soluble aromatic compound is suppressed,
can be obtained.

The present invention can provide a composition containing (A) a hardly water-soluble aromatic compound which suppresses deposition of a hardly water-soluble aromatic compound in a solution where the concentration of the hardly water-soluble aromatic compound exceeds the saturation solubility thereof. Here, whether or not "deposition is suppressed" can be determined as follows. That is, if the deposition of the hardly water-soluble aromatic compound or the generation of the precipitate are not visually observed at 24 hours' time after the preparation of the composition containing the hardly water-soluble aromatic compound by the present invention process, it can be determined that the deposition is suppressed.

The reason why the deposition of the hardly water-soluble aromatic compound is suppressed even if the hardly water-soluble aromatic compound exceeds the saturating solubility in the process for producing the present invention is not clear, but it can be considered as follows.

It can be considered that the presence of an aqueous medium containing water in the polyol and heating causes the hardly water-soluble aromatic compound to form a stable network structure by solvation with the polyol and water, and the structure is maintained even when diluted with water.

The method for producing a composition containing a hardly water-soluble aromatic compound is a method for production which includes:

Step (1) of obtaining a hardly water-soluble aromatic compound solution 1, Step (1) including Step (1-1) of preparing a material for heating comprising (A) a hardly water-soluble aromatic compound, (B) a polyol, and (C) an aqueous medium, and Step (1-2) of obtaining a heated solution containing a hardly water-soluble aromatic compound by heating the material for heating at normal pressure at a temperature of less than 100° C.; and Step (2) of obtaining a hardly water-soluble aromatic compound solution 2 by adding water to the hardly water-soluble aromatic compound solution 1 such that the hardly water-soluble aromatic compound solution 2 has a concentration of the (A) hardly water-soluble aromatic compound above a saturation solubility at 25° C., wherein, in Step (1), a content of a surfactant in the material for heating is 0.1 mass % or less and a content of the (A) hardly water-soluble aromatic compound in the material for heating is below a saturation solubility of the (A) hardly water-soluble aromatic compound in a solvent having the same composition at 25° C.

The method for producing a hardly water-soluble aromatic compound solution 1 is a method for production which includes:

Step (1-1) of preparing a material for heating comprising (A) a hardly water-soluble aromatic compound, (B) a polyol, and (C) an aqueous medium, and Step (1-2) of obtaining a heated solution containing a hardly water-soluble aromatic compound by heating the material for heating at normal pressure at a temperature of less than 100° C., wherein, in Step (1-2), the material for heating is heated in such a way that the (A) hardly water-soluble aromatic compound is prevented from deposition in a hardly water-soluble aromatic compound solution 2 that is obtained by diluting the hardly water-soluble aromatic compound solution 1 with water such that a concentration of the (A) hardly water-soluble aromatic compound is above a saturation solubility.

In this specification, the hardly water-soluble aromatic compound solution 1 is also referred to as "Solution 1", and the hardly water-soluble aromatic compound solution 2 is also referred to as "Solution 2".

[Step (1-1)]

This step of preparing a material for heating comprising (A) a hardly water-soluble aromatic compound, (B) a polyol, and (C) an aqueous medium.

As herein, the (A) hardly water-soluble aromatic compound means an aromatic compound having solubility of 3.0 g/L or less in water at 25° C. In the present invention, an aromatic compound having solubility of 2.5 g/L or less, and further 1.0 g/L or less, in water at 25° C. is preferably applicable.

An aromatic compound having solubility of 5 g/L or more, further 10 g/L or more, and further 20 g/L or more, in the (B) polyol at 25° C. is preferably applicable as the (A) hardly water-soluble aromatic compound.

The solubility herein refers to the number of grams of a solute dissolved in 1 L of a solution and expressed in a unit [g/L].

In view of effectively obtaining advantages of the present invention, the (A) hardly water-soluble aromatic compound in the present invention is such compound that alters by heat or that is difficult to handle at 100° C. or more due to volatility or sublimability etc.

The (A) hardly water-soluble aromatic compound is not particularly limited except the conditions described above, and examples thereof include an antibacterial component, a whitening component, and a hair growth component. The (A) hardly water-soluble aromatic compound may be a single compound or a mixture of two or more compounds.

Examples of the hardly water-soluble aromatic compound used as an antibacterial component include phenolic antibacterial agents. Examples of the phenolic antibacterial agent include chlorophenolic antibacterial agents such as triclosan, chlorothymol, carvacrol, chlorophen, dichlorophen, hexachlorophene, chloroxylenol, and chlorocresol; para-hydroxybenzoates (alkyl parabens) such as methyl parahydroxybenzoate (methyl paraben), ethyl parahydroxybenzoate (ethyl paraben), propyl parahydroxybenzoate (propyl paraben), isopropyl parahydroxybenzoate (isopropyl paraben), butyl parahydroxybenzoate (butyl paraben), isobutyl parahydroxybenzoate (isobutyl paraben), and benzyl parahydroxybenzoate (benzyl paraben); and o-phenylphenol, and isopropyl methylphenol. Of these, methyl paraben, ethyl paraben, and isopropyl methylphenol are preferable, and isopropyl methylphenol is more preferable, in view of high sublimability and effectively obtaining effects of the present invention.

Examples of the aromatic whitening component include chromone derivatives.

The chromone derivative is preferably a compound which has a linear or branched alkyl group having 1 to 15 carbon atoms at 2 position of a chromone, that is, 4H-1-benzopyran-4-one, and a hydrogen atom, a hydroxy group, or an alkoxy group at 7 position.

Examples of the chromone derivative include 2-butylchromone, 2-pentylchromone, 2-heptylchromone, 2-nonylchromone, 2-hexadecylchromone, 2-(1-ethylpentyl)chromone, 2-butyl-7-methoxychromone, 2-pentyl-7-methoxychromone, 2-heptyl-7-methoxychromone, 2-nonyl-7-methoxychromone, 2-pentadecyl-7-methoxychromone, 2-(1-ethylpentyl)-7-methoxychromone, 7-hydroxy-2-methylchromone, 7-hydroxy-2-butylchromone, 7-hydroxy-2-pentylchromone, 7-hydroxy-2-heptylchromone, 7-hydroxy-2-nonylchromone, 7-hydroxy-2-pentadecylchromone, and 7-hydroxy-2-(1-ethylpentyl)chromone. Of these, 2-(1-ethylpentyl)-7-methoxychromone is preferable in view of concerns about heat denaturation and decomposition and effectively obtaining effects of the present invention.

The chromone derivative can be produced by a known method such as the method described in JP-A-hei 7-188208.

Examples of the aromatic hair growth component include flavanonol derivatives such as trans-3,4'-dimethyl-3-hydroxyflavanone; nicotinic acids such as benzyl nicotinate, tocopherol nicotinate, and β-butoxyethyl nicotinate; vitamin Es such as α-tocopherol, DL-α-tocopherol acetate, tocopherol nicotinate, and natural vitamin E; and minoxidil, bimatoprost, tafluprost, nonanoic acid vanillylamide, St. John's wort extracts, and capsicum tincture.

Especially, trans-3,4'-dimethyl-3-hydroxyflavanone, tocopherol nicotinate, α-tocopherol, DL-α-tocopherol acetate, and natural vitamin E are particularly preferable, and trans-3,4'-dimethyl-3-hydroxyflavanone is more preferable, considering heat denaturation and decomposition and effectively obtaining effects of the present invention. The flavanonol derivative can be produced by a known method such as the method described in JP-A-2000-198779.

Of these components, these used as an antibacterial component, particularly phenolic antibacterial components, are preferable, and para-hydroxybenzoates and isopropyl methylphenols are more preferable, in view of concerns about heat denaturation and decomposition and effectively obtaining effects of the present invention. Particularly, methyl paraben, ethyl paraben, and isopropyl methylphenol are further preferable, and isopropyl methylphenol is furthermore preferable, in view of high sublimability and effectively obtaining affects of the present invention.

In the present invention, the content of the (A) hardly water-soluble aromatic compound in the material for heating is below the saturation solubility (25° C.) of the (A) hardly water-soluble aromatic compound in a solvent having the same composition. When the (A) hardly water-soluble aromatic compound is included in the material for heating in an amount below the saturation solubility (25° C.), the stability in a dissolved state of the (A) hardly water-soluble aromatic compound is enhanced in Solution 1 after the heated solution obtained in Step (1-2) is cooled. The content of the (A) hardly water-soluble aromatic compound in the material for heating is preferably 98 mass % or less, more preferably 95 mass % or less, and further preferably 90 mass % or less, of the saturation solubility (25° C.). In view of productivity per batch, the content of the (A) hardly water-soluble aromatic compound in the material for heating is preferably 52 mass % or more, more preferably 60 mass % or more, and further preferably 76 mass % or more, of the saturation solubility (25° C.).

The content of the (A) hardly water-soluble aromatic compound in the material for heating is preferably from 52 to 98 mass % more preferably from 60 to 95 mass %, and further preferably from 76 to 90 mass %, of the saturation solubility (25° C.).

The content of the (A) hardly water-soluble aromatic compound in the material for heating varies dependent on the kind but it is, in view of productivity per batch, preferably 1 mass % or more, more preferably 2 mass % or more, further preferably 3 mass % or more, and furthermore preferably 4 mass % or more, and in view of the stability in a dissolved state of the (A) hardly water-soluble aromatic compound after it is heated and in view of curtailing heating time, preferably 30 mass % or less, more preferably 25 mass % or less, further preferably 20 mass % or less, further preferably 17 mass % or less, and further preferably 15 mass % or less.

The content of the (A) hardly water-soluble aromatic compound in the material for heating is preferably from 1 to 30 mass %, more preferably from 2 to 25 mass %, further preferably from 3 to 20 mass %, furthermore preferably from 4 to 17 mass % and even more preferably from 4 to 15 mass %.

The (B) polyol used in the present invention is a collective term for alcohols in which two or more hydrogens in hydrocarbon are replaced with hydroxyl groups. The polyol preferably has solubility of 3.0 g/L or more, further preferably 3.5 g/L or more, and further preferably 4.0 g/L or more, in water at 25° C., and a polyol soluble in water at any ratio is furthermore preferable.

Examples of the (B) polyol include dihydric alcohols, trihydric alcohols, and condensates thereof, and specifically include alkylene glycols being dihydric alcohols, such as ethylene glycol, propylene glycol, 1,3-propanediol, and 1,3-butanediol; polyalkylene glycols being condensates of dihydric alcohols, such as diethylene glycol, dipropylene glycol, polyethylene glycol, and polypropylene glycol; glycerins and glycerin condensates such as glycerin, diglycerin, and triglycerin; and triols such as 1,2,4-butanetriol, 1,2,5-pentanetriol, 2-methylpropanetriol, 2-methyl-1,2,4-butanetriol, trimethylolethane, and trimethylolpropane. An average molecular weight of polyethylene glycol and polypropylene glycol is preferably 2,000 or less, more preferably 1,000 or less, and further preferably 400 or less. Of these, ethylene glycol, propylene glycol, 1,3-butanediol, dipropylene glycol, polyethylene glycol (molecular weight 400), glycerin, and diglycerin are more preferable, and propylene glycol, 1,3-butanediol, dipropylene glycol, polyethylene glycol (molecular weight 400), and glycerin are further preferable, in view of increasing a soluble amount of the (A) hardly water-soluble aromatic compound and causing the (A) hardly water-soluble aromatic compound in the material for heating to be a unsaturated state in Step (1).

The (B) polyol can be used singly or two or more can be used in combination.

The content of the (E) polyol in the material for heating can be adjusted according to the kind of the (C) aqueous medium to be described later.

In a case that the (C) aqueous medium does not include a monohydric alcohol, the content, of the (B) polyol in the material for heating is preferably 40 mass % or more, more preferably 50 mass % or more, and further preferably 60 mass % or more, in view of increasing a soluble amount of the (A) hardly water-soluble aromatic compound and causing the (A) hardly water-soluble aromatic compound in the material for heating to be a unsaturated state in Step (1). A smaller amount of the (B) polyol used is preferred from an economical viewpoint, and thus an upper limit is preferably 95 mass % or less, more preferably 90 mass % or less, and further preferably 85 mass % or less.

In a case that the (C) aqueous medium does not include a monohydric alcohol, the content of the (B) polyol in the material for heating is preferably from 40 to 95 mass %, more preferably from 50 to 90 mass %, and further preferably from 60 to 85 mass %.

On the other hand, when the (C) aqueous medium include a monohydric alcohol, the content of the (B) polyol in the material for heating is preferably 30 mass % or more, more preferably 35 mass % or more, and further preferably 45 mass % or more, in view of increasing a soluble amount of the (A) hardly water-soluble aromatic compound and causing the (A) hardly water-soluble aromatic compound in the material for heating to be a unsaturated state in Step (1). A smaller amount of the (B) polyol used is preferred from an economical viewpoint, and thus an upper limit is preferably 95 mass % or less, more preferably 90 mass % or less, and further preferably 85 mass % or less.

When the (C) aqueous medium includes a monohydric alcohol, the content of the (B) polyol in the material for heating is preferably from 30 to 95 mass %, more preferably from 35 to 90 mass %, and further preferably from 45 to 85 mass %.

In the present invention, a mass ratio of the (B) polyol to the (A) hardly water-soluble aromatic compound, (B)/(A), in the material for heating is preferably 1 or more, more preferably 1.5 or more, further preferably 2.0 or more, furthermore preferably 4 or more, and even more preferably 5 or more, in view of increasing a soluble amount of the (A) hardly water-soluble aromatic compound and causing the (A) hardly water-soluble aromatic compound in the material for heating to be a unsaturated state in Step (1). From an economical viewpoint, the mass ratio of (B)/(A) is preferably 80 or less, more preferably 40 or less, and more preferably 25 or less.

A mass ratio of the (B) polyol to the (A) hardly water-soluble aromatic compound, (B)/(A), in the material for heating is preferably from 1 to 80, more preferably from 1.5 to 40, further preferably from 2.0 to 40, furthermore preferably from 4 to 25, and even more preferably from 5 to 25.

The (C) aqueous medium used in the present invention refers to water and an aqueous solution of a monohydric alcohol. Examples of water include tap water, distilled water, ion-exchange water, and purified water.

The monohydric alcohol is not particularly limited as long as it mixes homogeneously with water. In view of usability as a raw material for a cosmetic product and high versatility, ethanol and propanol are more preferable, and ethanol is further preferable.

The content of the (C) water in the raw material for heating is preferably 2.0 mass % or more, more preferably 2.5 mass % or more, further preferably 3.0 mass % or more, and furthermore preferably 5.0 mass % or more, because the component (A) forms a network structure (hereinafter referred to as "molecular assemblies") by the solvation of the component (B) and the component (C) in Solution 1 to effectively prevent the deposition of the hardly water-soluble aromatic compound when Solution 1 is diluted with water to obtain Solution 2 in Step (2). In view of more effectively preventing the deposition of the hardly water-soluble aromatic compound when Solution 1 is diluted with water to obtain Solution 2 in Step (2) and in view of curtailing heating time and lowering a heating temperature in Step (1-2), the content of water as the component (C) in the material for heating is preferably 55 mass % or less, more preferably 48 mass % or less, further preferably 40 mass % or less, and furthermore preferably 30 mass % or less.

The content of the (C) water in the material for heating is preferably from 2.0 to 35 mass %, more preferably from 2.5 to 48 mass %, further preferably from 3.0 to 40 mass %, and furthermore preferably from 5.0 to 30 mass %.

In the present invention, when a monohydric alcohol is used as the component (C) in addition to the (B) polyol, the deposition of the hardly water-soluble aromatic compound is more effectively suppressed when Solution 1 is diluted with water to give Solution 2 in Step (2). This is presumably because the monohydric alcohol promotes the formation of molecular assemblies in Step (1-2) thereby facilitating Component (A) to be present in a stably dissolved state. For this reason, it is beneficial for a case where the (A) hardly water-soluble aromatic compound in the composition containing the same is highly concentrated and a case where a heating condition is eased.

When ethanol is used as Component (C), the content of ethanol in the material for heating is preferably 3 mass % or more, more preferably 5 mass % or more, further preferably 8 mass % or more, further preferably 13 mass % or more, and further preferably 20 mass % or more, in view of more effectively preventing the deposition of the hardly water-soluble aromatic compound in Solution 2 obtained by diluting Solution 1 with water in Step (2), and preferably 40 mass % or less, more preferably 30 mass % or less, further preferably 25 mass % or less, further preferably 22 mass % or less, and further preferably 20 mass % or less from an economical viewpoint.

The content of ethanol in the material for heating is preferably from 3 to 40 mass %, more preferably from 5 to 30 mass %, further preferably from 8 to 25 mass %, and furthermore preferably from 13 to 22 mass %, in view of more effectively preventing the deposition of the hardly water-soluble aromatic compound in Solution 2 obtained by diluting Solution 1 with water in Step (2) and from an economical viewpoint. When a monohydric alcohol other than ethanol is used as Component (C), the content of the monohydric alcohol in the material for heating is also preferably in the same ranges.

On the other hand, ethanol is skin irritant and thus when an amount of ethanol used is decreased in view of relieving the skin irritation, the content of ethanol in the material for heating is preferably 0 to 40 mass %, more preferably 0 to 10 mass %, further preferably 0 to 1 mass %, and further substantially 0 mass %, that is, it is preferable to include no ethanol.

In the present invention, a mass ratio of the (B) polyol to a total mass of the (B) polyol and the (C) aqueous medium, (B)/[(B)+(C)], in the material for heating is preferably from 0.45 to 0.98, more preferably from 0.48 to 0.96, and further preferably from 0.51 to 0.95, in view of forming molecular assemblies and causing the Component. (A) to be present in a stably dissolved state, curtailing heating time and lowering a heating temperature in Step (1-2).

From the same viewpoint, when the (C) aqueous medium does not include any monohydric alcohol, a mass ratio of the (B) polyol to a total mass of the (B) polyol and the (C) aqueous medium, (B)/[(B)+(C)], in the material for heating is preferably from 0.55 to 0.98, more preferably from 0.60 to 0.96, and further preferably from 0.65 to 0.95.

When the (C) aqueous medium includes a monohydric alcohol, a mass ratio of the (B) polyol to a total mass of the (B) polyol and the (C) aqueous medium, (B)/[(B)+(C)], in the material for heating is, from the same viewpoint, preferably from 0.53 to 0.80, more preferably from 0.55 to 0.75, and further preferably from 0.59 to 0.67.

The material for heating may suitably include other components in addition to the above Components (A) to (C) as long as the effects of the present invention are not affected; however, in view of maintaining the function of the (A) hardly water-soluble aromatic compound and relieving the skin irritation, the content of a surfactant in the material for heating is preferably 0.1 mass % or less, more preferably from 0 to 0.05 mass %, further preferably from 0 to 0.01 mass %, and furthermore preferably substantially 0 mass %, that is, it is preferable to include no surfactant.

[Step (1-2)]

This is a step of obtaining a hardly water-soluble aromatic compound-containing heated solution by heating the material for heating at normal pressure at a temperature of less than 100° C. Step (1-2) may be carried out after Step (1-1) or may be carried out simultaneously with Step (1-1). When heating is carried out at normal pressure without applying a pressure, heating does not require a special apparatus such as a pressure and heat resistant container, and heating carried out at less than 100° C. is preferably applicable against heat alteration of the hardly water-soluble aromatic compound and volatile or sublimable hardly water-soluble aromatic compound.

A heating temperature is less than 100° C.; however, in view of curtailing heating time and in view of the stability in a dissolved state of the (A) hardly water-soluble aromatic compound in Solution 2 obtained by diluting Solution 1 with water in Step (2), a heating temperature is preferably 50° C. or more, more preferably 55° C. or more, further preferably 60° C. or more, further preferably 65° C. or more, further preferably 70° C. or more, further preferably 75° C. or more, and further preferably 80° C. or more. Additionally, a heating temperature is preferably 98° C. or less, more preferably 95° C. or less, further preferably 90° C. or less, furthermore preferably 85° C. or less, and even more preferably 80° C. or less, in view of preventing the heat alteration of the hardly water-soluble aromatic compound.

A heating temperature is preferably from 50 to less than 100° C., more preferably from 55 to 98° C., further preferably from 60 to 95° C., furthermore preferably from 65 to 90° C., and even more preferably from 70 to 85° C.

A heating temperature is preferably is 50 to less than 100° C., more preferably from 60 to 98° C., further preferably from 70 to 95° C., and furthermore preferably from 80 to 95° C., particularly in view of curtailing heating time and in view of the stability in a dissolved state of the (A) hardly water-soluble aromatic compound in Solution 2 obtained by diluting Solution 1 with water in Step (2), and is preferably from 50 to 98° C., more preferably from 55 to 90° C., further preferably from 60 to 85° C., and furthermore preferably from 65 to 80° C., particularly in view of preventing the heat alteration of the hardly water-soluble aromatic compound.

Heating time varies depending on the heating temperature and the like and thus may not be necessarily generalized. In view of the stability in a dissolved state of the (A) hardly water-soluble aromatic compound in Solution 2 obtained by diluting Solution 1 with water in Step (2), heating time is preferably 6 minutes or more, more preferably 12 minutes or more, further preferably 18 minutes or more, and further preferably 24 minutes or more, and in view of productivity, preferably 120 hours or less, more preferably 48 hours or less, further preferably 24 hours or less, and further preferably 8 hours or less.

Heating time is preferably 6 minutes or more and 120 hours or less, more preferably 12 minutes or more and 18 hours or less, further preferably 18 minutes or more and 24 hours or less, and further preferably 24 minutes or more and 8 hours or less.

In the present invention, the heating time refers to the length of time during which the temperature of the material for heating is at a predetermined heating temperature.

The heating conditions in Step (1-2) are to heat the material for heating such that the (A) hardly water-soluble aromatic compound is prevented from deposition in Solution 2 obtained by diluting Solution 1 with water in Step (2), that is, a solution of Solution 1 diluted with water such that the concentration of the (A) hardly water-soluble aromatic compound is above the saturation solubility. It can be considered that a state in which the (A) hardly water-soluble aromatic compound is less likely to deposit in Solution 2 obtained by diluting Solution 1 with water in Step (2) by applying sufficient heat to the (A) hardly water-soluble aromatic compound, the (B) polyol, and the (C) aqueous medium all of which are present together. For this reason, it is required to give sufficient thermal history to the material for heating in order to stabilize the dissolved state of the (A) hardly water-soluble aromatic compound without causing deposition. Examples of the means for giving sufficient thermal history to the material for heating include elevating a heating temperature and extending heating time, depending on a composition of the material for heating.

For example, in a case where the content of the (A) hardly water-soluble aromatic compound is same and the kinds and contents of the (B) polyol and the (C) aqueous medium are same in the material for heating, when a heating temperature is low (e.g., 50° C. or more and less than 75° C.), heating time car be longer than when a heating temperature is higher, and when a heating temperature is high (e.g., 75° C. or more and less than 100° C.), heating time can be shorter than when a heating temperature is lower.

In a case where heating temperatures are same and where the kinds and contents of the (B) polyol and the (C) aqueous medium are same, when the content of the (A) hardly water-soluble aromatic compound in the material for heating is high (e.g., more than 13 mass %), heating time can be longer than when the content of the (A) hardly water-soluble aromatic compound is lower; when the content of the (A) hardly water-soluble aromatic compound in the material for heating is moderate (e.g., more than 8 mass % and 13 mass % or less), heating time can be longer than when the content of the (A) hardly water-soluble aromatic compound is lower but shorter than when such the content is higher; and the content of the (A) hardly water-soluble aromatic compound in the material for heating is low (e.g., 8 mass % or less), heating time can be shorter than when the content of the (A) hardly water-soluble aromatic compound is higher.

For cases where contents of the (A) hardly water-soluble aromatic compound are same and the kinds, where contents of the (B) polyol are same in the material for heating and where heating temperatures are same, when the (C) aqueous medium is water, heating time can be longer than when the (C) aqueous medium is an aqueous solution of a monohydric alcohol, and when the (C) aqueous medium is an aqueous solution of a monohydric alcohol, heating time can be shorter than when the (C) aqueous medium is water.

In Step (1-2), the optimum condition in terms of preventing the deposition of the (A) hardly water-soluble aromatic compound in Solution 2 obtained in Step (2) varies depending on the balance between the composition composed of Components (A) to (C), the heating temperature, and the heating time as described above. It is preferable to suitably adjust the heating temperature and the heating time according to the composition composed of Components (A) to (C); the range of Step (1-2) can be clarified by arranging various variables. Specifically, factors pertaining to such a composition and heating conditions, are specified and preferable ranges for heating conditions are established by parameters in view of forming molecular assemblies in Solution 1 and the stability in a dissolved state of the (A) hardly water-soluble aromatic compound in Solution 2 diluted with water. The following describes the procedure for developing parameter establishment.

1. Specifying Factors

In the present invention, it is necessary to create a state in which Component (A) is stably dissolved in Solution 1 via Step (1-2), and "Dissolution State Index: Y" is set as an index for such a dissolved state. Y is a parameter covering factors pertaining to a dissolved state of Component (A) as a subject. Factors significantly pertaining to Y include "Concentration of Component (A): $C_0$" in the material for heating obtained in Step (1-1) and "saturation solubility of Component (A): $C_s$" in the solvent of Components (B) and (C). As $C_s$ largely fluctuates by temperature changes, an impact by "Heating Temperature: T" in Step (1-2) should also be considered. Temperature changes cause impacts predominantly on the solubility of Component (A) and the viscosity of the solution in which Compound (A) is dissolved, that is, the dispersibility of Compound (A), and thus the solubility and dispersibility of Component (A) by temperature changes are set as "Dissolution Efficiency: E" (the factor including T). It is thus concluded that Y can be expressed with $C_0$, $C_s$, and E.

The heating conditions include "Treatment Time: t" and it is considered that the above Y changes depending on the length thereof. For this reason, parameters on the optimum heating conditions are established by arranging the relation between the above Y and t in embodiments of the present invention.

2. Establishment of Dissolution Efficiency E

Solubility and dispersibility cause impacts on the dissolution efficiency. Thus, $E_{sol}$ is set as a term for the solubility and $E_{dis}$ is set as a term for the dispersibility, respectively. Described hereinafter is the establishment of Dissolution Efficiency E in a case of using i) isopropyl methylphenol as Component (A), 1,3-butanediol as Component (B), and water as Component (C).

2-1. Establishment of $E_{sol}$ $E_{sol}$ is determined based on a ratio of Component (B) to the solvent in which Component (A) is dissolved and a treatment temperature. Solubility of Component (A) is first measured by changing ratios of Component (B) to the solvent and temperatures thereof. Solvent concentration: $C_{BG}$ (concentration of Component (B) in Component (B)+ Component (C)) is plotted along the abscissa, whereas solubility of Component (A) in the solvent is plotted along the ordinate. A graph solubility relative to the temperature is thus drawn by changing solvent concentrations and treatment temperatures. When an approximate expression is used, solubility: S can be represented by the following (Equation 1), where A and B are constants.

$$S = Ae\hat{\ }(BC_{BG}) \qquad \text{(Equation 1)}$$

When both A and B are reorganized as functions of the temperature, solubility of Component (A) can be derived as an estimated solubility: S' from $C_{BG}$ and Treatment Temperature T as shown in the following (Equation 2).

$$S' = (0.002e^{0.06T})e\hat{\ }\{(-0.0001T0.08)C_{BG}\} \qquad \text{(Equation 2)}$$

$E_{sol}$ herein can be expressed as solubility obtained by dividing S' by the original dissolved amount, that is, solubility of Component (A) at room temperature S". Because of S"=0.086e^(0.085$C_{BG}$), $E_{sol}$ can be represented by the following (Equation 3).

$$E_{sol} = \frac{S'}{S''} = \left\{\frac{0.023}{e^{0.085C_{BG}}}e^{0.06T}\right\}e^{\{-0.0001T+0.08\}C_{BG}} \qquad \text{(Equation 3)}$$

2-2. Establishment of $E_{dis}$

In the same manner as $E_{sol}$, $E_{dis}$ is determined based on a ratio of Component (B) to the solvent in which Component (A) is dissolved and a treatment temperature. Viscosity as the dispersibility of the solvent is first supposed to be evaluated and solvent viscosity is measured by changing ratios of Component (B) to the solvent and temperatures thereof. Solvent concentration: $C_{BG}$ (concentration of Component (B) in Component (B)+Component (C)) is plotted along the abscissa, whereas solvent viscosity is plotted along the ordinate. A viscosity graph by the temperature is thus drawn. With an approximate expression. Dispersibility: D can be represented by the following (Equation 4), where A and B are constants.

$$D = Ae\hat{\ }(BC_{BG}) \qquad \text{(Equation 4)}$$

When both A and B are reorganized as functions of the temperature, a solvent viscosity can be derived as an estimated dispersibility: D' from $C_{BG}$ and Treatment Temperature T as shown in the following (Equation 5).

$$D' = (0.0012e^{0.014T})e\hat{\ }\{(-0.00057T+0.48)C_{BG}\} \qquad \text{(Equation 5)}$$

$E_{dis}$ herein can be expressed as a dispersibility obtained by dividing D' by a value of the predicted lowest solution viscosity, that is, the value of viscosity at the maximum temperature of the solvent, having the lowest solvent concentration. Because of D"=0.0003, $E_{dis}$ can be represented by the following (Equation 6).

$$E_{dis} = \frac{D'}{D''} = \frac{1}{0.003}\{0.0012e^{0.014T}\}e^{\{-0.00057T+0.048\}C_{BG}} \qquad \text{(Equation 6)}$$
$$= \{0.4e^{0.014 \times T}\}e^{\{-0.00057T+0.048\}C_{BG}}$$

2-3. Establishment of E

The higher a temperature is, the higher value the above $E_{sol}$ shows, and the higher a temperature is, the lower $E_{dis}$ shows. For this reason, one of Dissolution Efficiency E can be defined as $E = E_{dis}/E_{sol}$. E can be represented as shown in the following (Equation 7) from the above (Equation 3) and (Equation 6).

$$E = \frac{E_{dis}}{E_{sol}} = \frac{\{0.4e^{0.014T}\}}{\left\{\frac{0.023}{e^{0.085C_{BG}}}e^{0.06T}\right\}}e^{\{-0.046T\}}e^{\{-0.00047C_{BG}-0.032C_{BG}\}} \qquad \text{(Equation 7)}$$
$$= [17.4e^{0.085C_{BG}}e^{\{-0.046T\}}]e^{\{-0.00047TC_{BG}-0.032C_{BG}\}}$$

3. Establishment of Dissolution State Index Y

"Saturation ratio ($C_0/C_s$)" can be used as an index for concluding that Component (A) is stably dissolved in the solution. For a highly crystalline material such as a hardly water-soluble material, a feed concentration $C_0$ significantly causes an impact on a dissolved state, and hence correction is made by further multiplying a saturation ratio by $C_0$. It is thus concluded that Dissolution State Index Y is represented by the following (Equation 8) when expressed with the above E, $C_0$, and $C_s$.

$$Y = \frac{C_0^2}{C_s} \times E = \qquad \text{(Equation 8)}$$
$$\frac{C_0^2}{C_s} \times [17.4e^{0.085C_{BG}}e^{\{-0.046T\}}]e^{\{-0.00047TC_{BG}-0.032C_{BG}\}}$$

4. Establishment of Parameter Definition

Subsequently, the relation between Dissolution State Index Y and heating time is determined. Actually, carrying out experiments by changing a composition composed of isopropyl methylphenol as Component (A), 1,3-butanediol as Component (B), and water as Component (C) and temperatures enables to determine a relational expression from about 10 to 20 pieces of experimental data.

Figure 1:
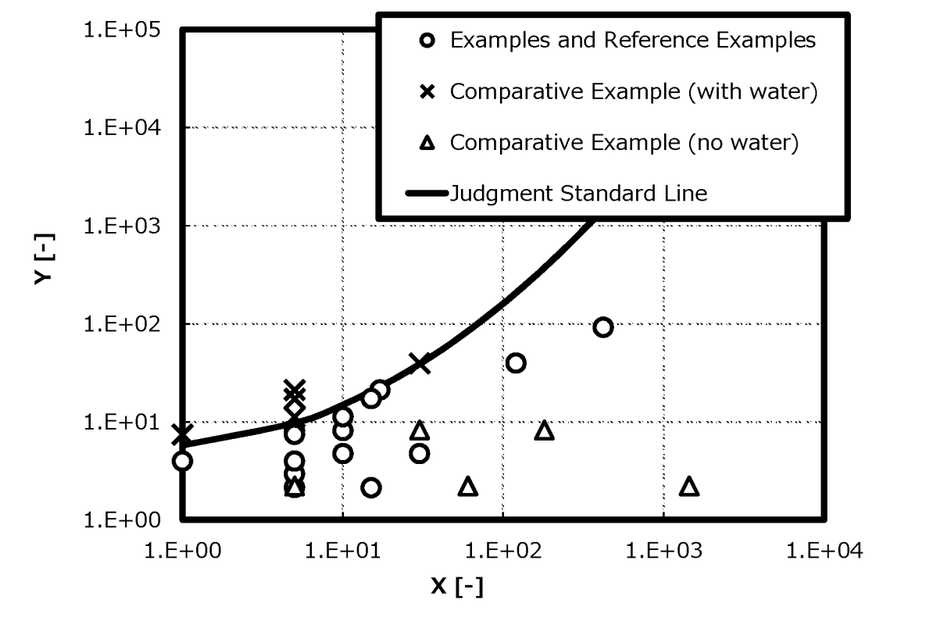
Figure 1 The judgment standard line for judging the presence or absence of deposition of (A) a hardly water-soluble aromatic compound or the generation of a precipitate is shown.

As shown in FIG. 1, various experiments were carried out by compositions of Components (A) to (C), heating temperatures, and heating period of time, and the results on deposition and precipitation of the (A) hardly water-soluble aromatic compound in Solution 2, are plotted on a graph, assuming the X-axis as the heating time and the Y-axis as Dissolution State Index Y. From the results of FIG. 1, a region where the effect of the present invention can be obtained, that is, a boundary Z between the regions where the deposition and precipitates do not occur and occur can be represented by the following (Equation 9).

i) $Z=0.006t^2+0.95t+4.8$ (Equation 9)

(where t represents heating time.)

When Y<Z is satisfied, the effect of the present invention can be obtained, and when Y≥Z is satisfied, the effect of the present invention may not be obtained.

Thus, when Y and Z are once determined by the first experiment, a heating temperature and heating time with which the effect of the present invention can be obtained can be selected for the composition composed of Components (A) to (C). Then, Y and Z can also be determined by the same method for cases of combinations other than the combination of isopropyl methylphenol as Component (A), 1,3-butanediol as Component (B), and water as Component (C), whereby a suitable heating temperature and heating time to obtain the effect of the present invention can be selected.

When isopropyl methylphenol is used as Component (A) with Component (B) including a polyol other than 1,3-butanediol and/or Component (C) including an aqueous solution of a monohydric alcohol, Y' can also be determined simply by using E, which is used when deriving (Equation 9) determined for 1,3-butanediol as Component (B) and water as Component (C) described above. For the compositions shown below, Zs derived from Y' are shown below.

ii) When Component (B) is 1,3-butanediol and Component (C) is water and ethanol $Z=0.001X^2+4.7X+15$ (Equation 10)

iii) When Component (B) includes a polyol other than 1,3-butanediol and Component (C) is water $Z=0.017X^2+0.24X+2.7$ (Equation 11)

iv) When Component (B) includes a polyol other than 1,3-butanediol and Component (C) is water and ethanol.

$Z=0.28X^2+3.85X+0.14$ (Equation 12)

Hereinafter, preferable examples of the present Step (1-2) are shown when a phenolic antibacterial agent is used as the (A) hardly water-soluble aromatic compound.

To heat a material for heating comprising 1 to 7.5 mass % of a phenolic antibacterial agent, 60 to 95 mass % of (B) a polyol, and 1 to 39 mass % of (C) water at from 70 to 99° C. for 1 minute or more.

To heat a material for heating comprising 1 to 6.0 mass % of a phenolic antibacterial agent, 65 to 95 mass % of (B) a polyol, and 1 to 34 mass % of (C) water at from 75 to 99° C. for 1 minute or more.

To heat a material for heating comprising 1 to 5.5 mass % of a phenolic antibacterial agent, 70 to 95 mass % of (B) a polyol, and 1 to 29 mass % of (C) water at from 80 to 99° C. for 1 minute or more.

To heat a material for heating comprising 1 to 7.5 mass % of a phenolic antibacterial agent, 60 to 95 mass % of (B) a polyol, and 1 to 39 mass % of (C) water at from 50 to 99° C. for 15 minutes or more.

To heat a material for heating comprising 1 to 6.0 mass % of a phenolic antibacterial agent, 65 to 95 mass % of (B) a polyol, and 1 to 34 mass % of (C) water at from 55 to 99° C. for 15 minutes or more.

To heat a material for heating comprising 1 to 5.5 mass % of a phenolic antibacterial agent, 70 to 95 mass % of (B) a polyol, and 1 to 29 mass % of (C) water at from 60 to 99° C. for 15 minutes or more.

To heat a material for heating comprising 5.5 to 12.5 mass % of a phenolic antibacterial agent, 60 to 93.5 mass % of (B) a polyol, and 1 to 34.5 mass % of (C) water at from 70 to 99° C. for 10 minutes or more.

To heat a material for heating comprising 5.5 to 12.0 mass % of a phenolic antibacterial agent, 65 to 93.5 mass % of (B) a polyol, and 1 to 29.5 mass % of (C) water at from 75 to 99° C. for 10 minutes or more.

To heat a material for heating comprising 5.5 to 11.5 mass % of a phenolic antibacterial agent, 70 to 93.5 mass % of (B) a polyol, and 1 to 24.5 mass % of (C) water at from 80 to 99° C. for 10 minutes or more.

To heat a material for heating comprising 5.5 to 12.5 mass % of a phenolic antibacterial agent, 60 to 93.5 mass % of (B) a polyol, and 1 to 34.5 mass % of (C) water at 50 to 99° C. for 30 minutes or more.

To heat a material for heating comprising 5.5 to 12.0 mass % of a phenolic antibacterial agent, 65 to 93.5 mass % of (B) a polyol, and 1 to 29.5 mass % of (C) water at 55 to 99° C. for 30 minutes or more.

To heat a material for heating comprising 5.5 to 11.5 mass % of a phenolic antibacterial agent, 70 to 93.5 mass % of (B) a polyol, and 1 to 24.5 mass % of (C) water at from 60 to 99° C. for 30 minutes or more.

To heat a material for heating comprising 11.5 to 18 mass % of a phenolic antibacterial agent, 60 to 87.5 mass % of (B) a polyol, and 1 to 28.5 mass % of (C) water at from 85 to 99° C. for 5 minutes or more.

To heat a material for heating comprising mass % of a phenolic antibacterial agent, 65 to 87.5 mass % of (B) a polyol, and 1 to 23.5 mass % of (C) water at from 87.5 to 99° C. for 5 minutes or more.

To heat a material for heating comprising 11.5 to 16 mass % of a phenolic antibacterial agent, 70 to 87.5 mass % of (B) a polyol, and 1 to 18.5 mass % of (C) water at from 90 to 99° C. for 5 minutes or more.

To heat a material for heating comprising 11.5 to 18 mass % of a phenolic antibacterial agent, 60 to 87.5 mass % of (B) a polyol, and 1 to 28.5 mass % of (C) water at from 75 to 99° C. for 15 minutes or more.

To heat a material for heating comprising 11.5 to 17 mass % of a phenolic antibacterial agent, 65 to 87.5 mass % of (B) a polyol, and 1 to 23.5 mass % of (C) water at from 77.5 to 99° C. for 15 minutes or more.

To heat a material for heating comprising 11.5 to 16 mass % of a phenolic antibacterial agent, 70 to 87.5 mass % of (B) a polyol, and 1 to 18.5 mass % of (C) water at from 80 to 99° C. for 15 minutes or more.

To heat a material for heating comprising 11.5 to 18 mass % of a phenolic antibacterial agent, 60 to 87.5 mass % of (B) a polyol, and 1 to 28.5 mass % of (C) water at from 50 to 99° C. for 120 minutes or more.

To heat a material for heating comprising 11.5 to 17 mass % of a phenolic antibacterial agent, 65 to 87.5 mass of (B)

a polyol, and 1 to 18.5 mass % of (C) water at from 55 to 99° C. for 120 minutes or more.

To heat a material for heating comprising 11.5 to 16 mass % of a phenolic antibacterial agent, 70 to 87.5 mass % of (B) a polyol, and 1 to 13.5 mass % of (C) water at from 60 to 99° C. for 120 minutes or more.

To heat a material for heating comprising 1 to 7.5 mass % of a phenolic antibacterial agent, 30 to 95 mass % of (B) a polyol, and 1 to 25 mass % of ethanol and 1 to 40 mass % of water as (C) an aqueous medium at from 50 to 99° C. for 1 minute or more.

To heat a material for heating comprising 1 to 6.0 mass % of a phenolic antibacterial agent, 35 to 90 mass % of (B) a polyol, and 2 to 25 mass % of ethanol and 1 to 40 mass % of water as (C) an aqueous medium at 50 to 99° C. for 5 minutes or more.

To heat a material for heating comprising 1 to 5.5 mass % of a phenolic antibacterial agent, 40 to 85 mass % of (B) a polyol, and 3 to 25 mass % of ethanol and 1 to 40 mass % of water as (C) an aqueous medium at 50 to 99° C. for 10 minutes or more.

To heat a material for heating comprising 5.5 to 12.0 mass % of a phenolic antibacterial agent, 35 to 90 mass % of (B) a polyol, and 3 to 25 mass % of ethanol and 1 to 40 mass % of water as (C) an aqueous medium at from 55 to 99° C. for 5 minutes or more.

To heat a material for heating comprising 5.5 to 11.5 mass % of a phenolic antibacterial agent, 40 to 85 mass % of (B) a polyol, and 5 to 25 mass % of ethanol and 1 to 40 mass % of water as (C) an aqueous medium at from 60 to 99° C. for 15 minutes or more.

To heat a material for heating comprising 11.5 to 18 mass % of a phenolic antibacterial agent, 30 to 85 mass % of (B) a polyol, and 1 to 25 mass % of ethanol and 1 to 30 mass % of water as (C) an aqueous medium at from 70 to 99° C. for 1 minute or more.

To heat a material for heating comprising 11.5 to 17 mass % of a phenolic antibacterial agent, 35 to 80 mass % of (B) a polyol, and 5 to 25 mass %, of ethanol and 1 to 25 mass % of water as (C) an aqueous medium at from 75 to 99° C. for 1 minute or more.

To heat a material for heating comprising 11.5 to 16 mass % of a phenolic antibacterial agent, 40 to 75 mass % of (B) a polyol, and 10 to 25 mass %, of ethanol and 1 to 20 mass % of water as (C) an aqueous medium at from 80 to 99° C. for 1 minute or more.

To heat a material for heating comprising 11.5 to 18 mass % of a phenolic antibacterial agent, 30 to 85 mass % of (B) a polyol, and 1 to 25 mass % of ethanol and 1 to 30 mass % of water as (C) an aqueous medium at from 50 to 99° C. for 7 minutes or more.

To heat a material for heating comprising 11.5 to 17 mass % of a phenolic antibacterial agent, 35 to 80 mass % of (B) a polyol, and 5 to 25 mass % ethanol and 1 to 25 mass % of water as (C) an aqueous medium at from 55 to 99° C. for 10 minutes or more.

To heat a material for heating comprising 11.5 to 16 mass % of a phenolic antibacterial agent, 40 to 75 mass % of (B) a polyol, and 10 to 25 mass % of ethanol and 1 to 20 mass % of water as (C) an aqueous medium at from 60 to 99° C. for 15 minutes or more.

To heat a material for heating comprising 16 to 36 mass % of a phenolic antibacterial agent, 30 to 80 mass % of (E) a polyol, and 1 to 25 mass % of ethanol and 1 to 30 mass % of water as (C) aqueous media at from 70 to 99° C. for 5 minutes or more.

To heat a material for heating comprising 16 to 32 mass % of a phenolic antibacterial agent, 35 to 75 mass % of (B) a polyol, and 5 to 25 mass % of ethanol and 1 to 25 mass % of water as (C) aqueous media at from 75 to 99° C. for 5 minutes or more.

To heat a material for heating comprising 16 to 28 mass % of a phenolic antibacterial agent, 40 to 70 mass % of (B) a polyol, and 10 to 25 mass % of ethanol and 1 to 20 mass % of water as (C) aqueous media at from 80 to 99° C. for 5 minutes or more.

To heat a material for heating comprising 16 to 36 mass % of a phenolic antibacterial agent, 30 to 80 mass % of (B) a polyol, and 1 to 25 mass % of ethanol and 1 to 30 mass % of water as (C) aqueous media at from 50 to 99° C. for 30 minutes or more.

To heat a material for heating comprising 16 to 32 mass % of a phenolic antibacterial agent, 35 to 75 mass % of (B) a polyol, and 5 to 25 mass % of ethanol and 1 to 25 mass % of water as (C) aqueous media at from 55 to 99° C. for 30 minutes or more.

To heat a material for heating comprising 16 to 28 mass % of a phenolic antibacterial agent, 40 to 70 mass % of (B) a polyol, and 10 to 25 mass % of ethanol and 1 to 20 mass % of water as (C) aqueous media at from 60 to 99° C. for 30 minutes or more.

Step (1-2) preferably includes a step of cooling the heated solution obtained after the material for heating is heated in order to obtain Solution 1. The cooling temperature is preferably from 0 to 50° C., more preferably from 0 to 35° C., and further preferably from 10 to 25° C., in view of stably obtaining Solution 1 and in view of effectively preventing the deposition of the hardly water-soluble aromatic compound in Solution 2 obtained by diluting Solution 1 with water.

The cooling rate of the heated solution calculated from the time required to lower to 25° C. from a heating temperature is preferably 0.01° C./s or more, more preferably 0.1° C./s or more, and further preferably 0.3° C./s or more, in view of stably obtaining Solution 1 and in view of effectively preventing the deposition of the hardly water-soluble aromatic compound in Solution 2 obtained by diluting Solution 1 with water.

In order to obtain Solution 1, Step (1-2) preferably includes a step of removing solid matters remained without being dissolved from the heated solution obtained after the material for heating is heated. The method for removing solid matters is not particularly limited and examples include centrifugation, decantation, and filtration.

Solution 1 obtained by Step (1) of the present invention is extremely stable and the hardly water-soluble aromatic compound does not deposit while stored. Thus, Solution 1 is stored as it is as an intermediate material without continuously carrying out, after Step (1), the subsequent Step (2), and Step (2) can be carried out at time of use. Step (2) is a step of adding water to Solution 1 to obtain Solution 2 such that Solution 2 has a concentration of the (A) hardly water-soluble aromatic compound above the saturation solubility at 25° C. and thus the composition containing the hardly water-soluble aromatic compound produced by the present invention has a large volume. Thus, when Solution 1 obtained by Step (1) is transported as it is as an intermediate material, transportation costs can be reduced in addition to the above effect, hence effective. For this reason, it is preferable for the present invention, in view of the above effects, to handle Solution 1 obtained by Step (1) of the present invention as an intermediate material and practice the present invention by carrying out Step (2) when producing the composition containing the hardly water-soluble aromatic compound obtained by the present invention or when producing a product comprising such a composition, which is an embodiment of the present invention. Consequently, the present invention is a method for producing the hardly water-soluble aromatic compound solution 1.

Solution 1 obtained by Step (1) of the present invention is extremely stable, and it is preferable to contain a monohydric alcohol as a component corresponding to Component (B) and/or as Component (C) to prevent the deposition of the (A) hardly water-soluble aromatic compound in case a temperature fluctuates while stored (particularly, when exposed to a low temperature condition or the like).

[Step (2)]

This is a step of obtaining Solution 2 by adding water to the above hardly water-soluble aromatic compound solution 1 such that the hardly water-soluble aromatic compound solution 2 has a concentration of the (A) hardly water-soluble aromatic compound above the saturation solubility at 25° C. An amount of water to be added is more than the amount such that the (A) hardly water-soluble aromatic compound reaches a saturated state at 25° C. in the solvent consisting of the (B) polyol, the (C) solvent composed of aqueous medium and water added. Such an amount, varies depending on an amount of the (A) hardly water-soluble aromatic compound and a ratio of the (B) polyol to the (C) aqueous medium in Solution 1, and an amount of water to be added is calculated from a found value of the hardly water-soluble aromatic compound in the composition composed of components in Solution 1 and the concentration of the (A) hardly water-soluble aromatic compound in Solution 2 to which water is added. Additionally, an amount of water to be added is within a range in which the (A) hardly water-soluble aromatic compound does not deposit.

Specifically, it is preferable, in view of a potentially high function expression of the (A) hardly water-soluble aromatic compound, to dilute Solution 1 with water such that the concentration of the (A) hardly water-soluble aromatic compound is preferably from 1.5 to 6.0 times, more preferably from 1.5 to 5.0 times, and further preferably from 1.5 to 4.0 times as large as the saturation solubility (25° C.) of the (A) hardly water-soluble aromatic compound in a solvent having the same composition.

Consequently, a composition containing the hardly water-soluble aromatic compound can be obtained. In such a composition, the (A) hardly water-soluble aromatic compound is present at a higher concentration than the saturation solubility, and thus when the composition is used, it is expected that the function of the (A) hardly water-soluble aromatic compound is highly exhibited.

[Method for Producing Cosmetic Products]

Products of various fields such as cosmetic products, pharmaceutical products, quasi-drugs, and drinks and foods can be produced by adding other raw materials to Solution 2 obtained by Step (2) of the present invention.

When water is added to Solution 1 in Step (2), the other raw materials are added simultaneously thereby producing products such as the above cosmetic products and the like. In such a case. Solution 1 obtained in Step (1) is diluted with, for example, an aqueous medium including a polymer, and an organic solvent or an oil agent is further added thereto as needed such that the resulting mixture has a concentration of the (A) hardly water-soluble aromatic compound above the saturation solubility at 25° C.

For the production of cosmetic products, it is preferable, in view of a potential for highly expressing of the function of the (A) hardly water-soluble aromatic compound, to adjust the content of the hardly water-soluble aromatic compound such that the concentration of the (A) hardly water-soluble aromatic compound is preferably from 1.5 to 6.0 times as large as the saturation solubility (25° C.) of the (A) hardly water-soluble aromatic compound in a solvent having the same composition.

With respect to the embodiments described above, the present invention further discloses the following production methods.

<1> A method for producing a composition containing a hardly water-soluble aromatic compound, comprising:

Step (1) of obtaining a hardly water-soluble aromatic compound solution Step (1) including Step (1-1) of preparing a material for heating comprising (A) a hardly water-soluble aromatic compound, (B) a polyol, and (C) an aqueous medium, and Step (1-2) of obtaining a heated solution containing a hardly water-soluble aromatic compound by heating the material for heating at normal pressure at a temperature of less than 100° C.; and Step (2) of obtaining a hardly water-soluble aromatic compound solution 2 by adding water to the above solution 1 such that the hardly water-soluble aromatic compound solution 2 has a concentration of the (A) hardly water-soluble aromatic compound above a saturation solubility at 25° C., wherein in Step (1-1), in the material for heating, a mass ratio of the (B) polyol to a total mass of the (B) polyol and the (C) aqueous medium, (B)/[(B)+(C)], is from 0.45 to 0.93 and a mass ratio of the (B) polyol to the (A) hardly water-soluble aromatic compound, (B)/(A), is 1 or more and 80 or less, and in Step (1), a content of a surfactant in the material for heating is 0.1 mass % or less and a content of the (A) hardly water-soluble aromatic compound in the material for heating is below a saturation solubility of the (A) hardly water-soluble aromatic compound in a solvent having the same composition at 25° C.

<2> A method for producing a composition containing a hardly water-soluble aromatic compound, comprising:

Step (1) of obtaining a hardly water-soluble aromatic compound solution 1, Step (1) comprising Step (1-1) of preparing a material for heating comprising (A) a hardly water-soluble aromatic compound, (B) a polyol, and (C) an aqueous medium, and Step (1-2) of obtaining a heated solution containing a hardly water-soluble aromatic compound by heating the material for heating at normal pressure at a temperature of less than 100° C.; and Step (2) of obtaining a hardly water-soluble aromatic compound solution 2 by adding water to the above solution 1 such that the hardly water-soluble aromatic compound solution 2 has a concentration of the (A) hardly water-soluble aromatic compound above a saturation solubility at 25° C., wherein in Step (1-1), the (C) aqueous medium in the material for heating does not include any monohydric alcohol, and, in the material for heating, a content of the (B) polyol is from 40 to 95 mass % and a mass ratio of the (B) polyol to a total mass of the (B) polyol and the (C) aqueous medium, [(B)/((B)+(C))], is from 0.55 to 0.98, and in Step (1), a content of a surfactant in the material for heating is 0.1 mass % or less and a content of the (A) hardly water-soluble aromatic compound in the material for heating is below a saturation solubility of the (A) hardly water-soluble aromatic compound in a solvent having the same composition at 25° C.

<3> A method for producing a composition containing a hardly water-soluble aromatic compound, comprising:

Step (1) of obtaining a hardly water-soluble aromatic compound solution 1, Step (1) comprising Step (1-1) of preparing a material for heating comprising (A) a hardly water-soluble aromatic compound, (B) a polyol, and (C) an aqueous medium, and Step (1-2) of obtaining a heated solution containing a hardly water-soluble aromatic compound by heating the material for heating at normal pressure at a temperature of less than 100° C.; and Step (2) of obtaining a hardly water-soluble aromatic compound solution 2 by adding water to the above solution 1 such that the hardly water-soluble aromatic compound solution 2 has a concentration of the (A) hardly water-soluble aromatic compound above a saturation solubility at 25° C., wherein, in Step (1-1), the (C) aqueous medium in the material for heating does not include any monohydric alcohol, a content of the (B) polyol in the material for heating is from 40 to 95 mass %, and a mass ratio of the (B) polyol to the (A) hardly water-soluble aromatic compound, [(B)/(A)], in the material for heating is 1 or more and 80 or less, and wherein, in Step (1), a content of a surfactant in the material for heating is 0.1 mass % or less and a content of the (A) hardly water-soluble aromatic compound in the material for heating is below a saturation solubility the (A) hardly water-soluble aromatic compound in a solvent having the same composition at 25° C.

<4> A method for producing a composition containing a hardly water-soluble aromatic compound, comprising:

Step (1) of obtaining a hardly water-soluble aromatic compound solution Step (1) including Step (1-1) of preparing a material for heating comprising (A) a hardly water-soluble aromatic compound, (B) a polyol, and (C) an aqueous medium, and Step (1-2) of obtaining a heated solution containing a hardly water-soluble aromatic compound by heating the material for heating at normal pressure at a temperature of less than 100° C.; and, Step (2) of obtaining a hardly water-soluble aromatic compound solution 2 by adding water to the above solution 1 such that the hardly water-soluble aromatic compound solution 2 has a concentration of the (A) hardly water-soluble aromatic compound above a saturation solubility at 25° C., wherein in Step (1-1), in the material for heating, a content, of the (A) hardly water-soluble aromatic compound is from 1 to 20 mass %, the (C) aqueous medium does not contain any monohydric alcohol, a content thereof is from 2.0 to 55 mass %, and a content of the (B) polyol is from 40 to 95 mass %, and in Step (1), a content of a surfactant in the material for heating is 0.1 mass %, or less and a content of the (A) hardly water-soluble aromatic compound in the material for heating is below a saturation solubility of the (A) hardly water-soluble aromatic compound in a solvent having the same composition at 25° C.

<5> A method for producing a composition containing a hardly water-soluble aromatic compound, comprising:

Step (1) of obtaining a hardly water-soluble aromatic compound solution 1, Step (1) comprising Step (1-1) of preparing a material for heating comprising (A) a hardly water-soluble aromatic compound, (B) a polyol, and (C) an aqueous medium, and Step (1-2) of obtaining a heated solution containing a hardly water-soluble aromatic compound by heating the material for heating at normal pressure at a temperature of less than 100° C.; and, Step (2) of obtaining a hardly water-soluble aromatic compound solution 2 by adding water to the above solution 1 such that the hardly water-soluble aromatic compound solution 2 has a concentration of the (A) hardly water-soluble aromatic compound above a saturation solubility at 25° C., wherein the (C) aqueous medium in the material for heating does not contain any monohydric alcohol and a content thereof is from 2.0 to 4.0 mass %, and, in the material for heating, a content of the (B) polyol is from 50 to 90 mass % and a mass ratio of the (B) polyol to a total mass of the (B) polyol and the (C) aqueous medium, [(B)/((B)+(C))], is from 0.65 to 0.95, and in Step (1), a content of a surfactant in the material for heating is 0.1 mass % or less and a content of the (A) hardly water-soluble aromatic compound in the material for heating is below a saturation solubility of the (A) hardly water-soluble aromatic compound in a solvent having the same composition at 25° C.

<6> The method according to any one of <1> to <5>, wherein the (A) hardly water-soluble aromatic compound is an aromatic compound having solubility of 1.0 g/L or less in water at 25° C.

<7> The method according to any one of <1> to <6>, wherein the (A) hardly water-soluble aromatic compound is an aromatic compound having solubility of 20 g/L or more in polyol at 25° C.

<8> The method according to any one of <1> to <7>, wherein the (A) hardly water-soluble aromatic compound is a phenolic antibacterial agent.

<9> The method according to any one of <1> to <8>, wherein a content of the (A) hardly water-soluble aromatic compound in the material for heating is 98 mass % or less and 60 mass % or more of a saturation solubility (25° C.).

<10> The method according to any one of <1> to <9>, wherein the (B) polyol is at least one selected from the group consisting of propylene glycol, 1,3-butanediol, dipropylene glycol, and polyethylene glycol (molecular weight 400).

<11> The method according to any one of <1> to <10>, wherein the (C) aqueous medium is an aqueous solution of ethanol.

<12> The method according to any one of <1> to <11>, wherein a content of the surfactant in the material for heating is substantially 0 mass %, that is, the surfactant is not included.

<13> The method according to any one of <1> to <12>, wherein heating time in Step (1-2) is 6 minutes or more and 120 hours or less.

<14> The method according to any one of <1> to <13>, wherein a heating temperature in Step (1-2) is from 55 to 98° C.

<15> The method according to any one of <1> to <14>, wherein in Step (1-1), Component (B) is 1,3-butanediol and Component (C) is water, and, in the material for heating, a content of (C) water is from 2.0 to 40 mass %, a content of the (B) polyol is from 50 to 90 mass %, and a mass ratio of the (B) polyol to a total mass of the (B) polyol and the (C) aqueous medium, [(B)/((B)+(C))], is from 0.65 to 0.95, and the material for heating is heated in Step (1-2) under a condition that a relation between Dissolution State Index Y represented by the following (Equation 8) and heating time t satisfies the following (Equation 9):

$$\text{Dissolution Index } Y = \frac{C_0^2}{C_s} \times E = \quad \text{(Equation 8)}$$

$$\frac{C_0^2}{C_s} \times [17.4 e^{0.085 C_{BG}} e^{\{-0.046T\}}] e^{\{-0.00047 T C_{BG} - 0.032 C_{BG}\}}$$

$$Y < 0.006 t^2 + 0.95 t + 4.8 \quad \text{(Equation 9)}$$

wherein $C_0$ represents a concentration of Component (A), $C_s$ represents a saturation solubility of Component (A), and T and t represent a heating temperature and heating time, respectively, in Step (1-2).

<16> The method according to any one of <1> to <15>, wherein, in Step (2), water is added to the hardly water-soluble aromatic compound solution 1 such that a concentration of the (A) hardly water-soluble aromatic compound is from 1.5 to 6.0 times as large as a saturation solubility (25° C.) of the (A) hardly water-soluble aromatic compound in a solvent having the same composition.

<17> A method for producing a cosmetic product, comprising a step of adding the composition containing the hardly water-soluble aromatic compound, the composition obtained by the method of any one of <1> to <16>.

<18> A method for producing a cosmetic product, wherein the composition containing the hardly water-soluble aromatic compound, the composition obtained by the method of any one of <1> to <16> is a cosmetic product.

Example 1

[Raw Materials]
Isopropyl methylphenol (IPMP, manufactured by Osaka Kasei Co., Ltd., purity 100%)
Methyl p-hydroxybenzoate (MP, manufactured by FUJIFILM Wako Pure Chemical Corporation, purity 99.0%)
1,3-Butanediol (1,3-BG, manufactured by KH Neochem Co., Ltd., purity 100%)
Polyethylene glycol 400 (PEG400, manufactured by FUJIFILM Wako Pure Chemical Corporation, purity 100%)
Dipropylene glycol (CPG, manufactured by AGC Inc., purity 100%)
Propylene glycol (PG, manufactured by ADEKA Corporation, purity 100%)
Glycerin (GLY, manufactured by Kao Corporation, purity 100%)
Ethanol (EtOH, manufactured by FUJIFILM Wako Pure Chemical Corporation, purity 99.5%)

[Measurement of Isopropyl Methylphenol and Methyl P-Hydroxybenzoate]
Measurement was carried out by a gradient method using a Hitachi High Performance Liquid Chromatograph with a column Cadenza CD-C18 (4.6 mmφ×150 mm, 3 μm) manufactured by Imtakt Corporation attached at a column temperature of 40° C. Mobile phase liquid A was a 0.05 mol/L acetic acid aqueous solution and liquid B was acetonitrile, which were fed at 1.0 mL/min. The gradient conditions are as follows.

| Time (min) | Liquid A (%) | Liquid B (%) |
|---|---|---|
| 0 | 85 | 15 |
| 20 | 80 | 20 |
| 35 | 10 | 90 |
| 50 | 10 | 90 |
| 50.1 | 85 | 15 |
| 60 | 85 | 15 |

The injected amount of a sample was 10 μL, detection was quantitatively determined by an absorbance at a wavelength of 283 nm for isopropyl methylphenol and an absorbance at a wavelength of 254 nm for methyl p-hydroxybenzoate.

[Solubility Measurement of Isopropyl Methylphenol and Methyl P-Hydroxybenzoate]
An aqueous solution to which a predetermined concentration of the polyol was added was prepared, subsequently isopropyl methylphenol or methyl p-hydroxybenzoate was added until a suspended state was achieved. The slurry was stirred (stirrer, 500 r/min) at room temperature (25° C.) for 3 days, followed by separating solid matters by filtration using a PTFE filter having a pore sire of 0.2 μm, and a concentration in the solution was measured.

[Evaluation on Solubility in Solution 2]
The isopropyl methylphenol composition (25° C.) was weighed in a clear glass screw tube having a volume of 30 mL such that a concentration of isopropyl methylphenol in Solution 2 after Step (2) was 0.1 mass %, and a predetermined amount of water (25° C.) was added thereto. The resultant was then shaken for 60 seconds by hand to mix the isopropyl methylphenol composition and water to be homogeneous, thereby obtaining Solution 2. The obtained Solution 2 was stored at 25° C. At the time of 24 hours have passed since Step (2), a deposition state of precipitates in Solution 2 was visually observed.

In the same manner as the operation as described above, the methyl p-hydroxybenzoate composition was diluted with water such that a concentration of methyl p-hydroxybenzoate in Solution 2 was 0.5 mass %, and a deposition state of precipitates in Solution 2 was visually observed.

"A" represents a clear solution, and "b" represents precipitate(s) observed.

Solubilities of isopropyl methylphenol and methyl p-hydroxybenzoate in each component at 25° C. are as follows.
Isopropyl Methylphenol
  Water: 0.15 g/L
  1,3-Butanediol: 400 g/L
  Propylene glycol: 182 g/L
  Glycerin: 0.8 g/L
Methyl P-Hydroxybenzoate
  Water: 2.5 g/L Examples 1 to 13, Reference Examples 1 and 2

Isopropyl methylphenol, 1,3-butanediol, and purified water were blended together according to the compositions shown in Table 1-1 and the obtained material for heating was fed into a stainless steel batch reactor having an inner volume of 190 mL (manufactured by Nitto Koatsu Co.) to carry out heating under the heating conditions shown in Table 1-1. After having reached a temperature shown in the table, retention time shown in the table was given and cooling was carried out (cooling rate 0.3° C./s) to room temperature (25° C.) by immediately immersing the reactor in an ice bath. The immediately cooled solution was taken cut, and filtered using a PTFE filter having a pore size of 0.2 μm thereby obtaining Solution 1 of the isopropyl methylphenol compositions. Water was added thereto to obtain Solutions 2 after Solution 1 was stored still at room temperature (25° C.) for 60 minutes in Examples to 13 or at room temperature (25° C.) for 5 minutes in Reference Examples 1 and 2. Table 1-1 shows the compositions and evaluation results of Solution 2.

Comparative Examples 1 to 10

Solution 1 of the isopropyl methylphenol composition was obtained by carrying out the same operation as in Example 1, except for blending isopropyl methylphenol, 1,3-butanediol, and purified water together according to the compositions shown in Table 1-2. Solution 1 was stored still at room temperature (25° C.) for 5 minutes and subsequently diluted with water thereby obtaining Solutions 2. Table 1-2 shows the compositions and evaluation results of Solutions 2.

TABLE 1-1

| (Mass %) | | | Example | | | | | | | | | |
|---|---|---|---|---|---|---|---|---|---|---|---|---|
| | | | 1 | 2 | 3 | 4 | 5 | 6 | 7 | 8 | 9 |
| Composition of material for heating | (A) | IPMP | 5 | 5 | 3 | 5 | 5 | 5 | 10 | 10 | 10 |
| | (B) | 1,3-BG | 80 | 80 | 75 | 90 | 85 | 80 | 85 | 85 | 80 |
| | | PG | — | — | — | — | — | — | — | — | — |
| | | Gly | — | — | — | — | — | — | — | — | — |
| | (C) | Purified water | 15 | 15 | 22.0 | 5 | 10 | 15 | 5 | 5 | 10 |
| | (A) Saturation solubility (25° C.) | | 9.5 | 9.5 | 5.9 | 20.5 | 13.8 | 9.5 | 20.0 | 20.0 | 13.4 |
| | (B)/(A) | | 16.0 | 16.0 | 25.0 | 18.0 | 17.0 | 16.0 | 8.5 | 8.5 | 8.0 |
| Heating conditions | Temperature [° C.] | | 80 | 60 | 80 | 80 | 80 | 80 | 80 | 80 | 80 |
| | Time [min] | | 1 | 17 | 15 | 5 | 5 | 5 | 5 | 10 | 10 |
| Composition of dilute solution | (A) | IPMP | 0.10 | 0.10 | 0.10 | 0.10 | 1.10 | 0.10 | 0.10 | 0.10 | 0.10 |
| | (B) | 1,3-BG | 1.60 | 1.60 | 2.50 | 1.80 | 1.70 | 1.60 | 0.85 | 0.85 | 0.80 |
| | | 1,3-PG | — | — | — | — | — | — | — | — | — |
| | | Gly | — | — | — | — | — | — | — | — | — |
| | (C) | Water | 98.3 | 98.3 | 97.4 | 98.1 | 98.2 | 98.3 | 99.1 | 99.1 | 99.1 |
| | (A) Saturation solubility (25° C.) | | <0.04 | <0.04 | <0.04 | <0.04 | <0.04 | <0.04 | <0.04 | <0.04 | <0.04 |
| Evaluation on dissolubility | | | a | a | a | a | a | a | a | a | a |
| X Value | | | 1 | 17 | 15 | 5 | 5 | 5 | 5 | 10 | 10 |
| Y Value | | | 3.96 | 21.07 | 2.12 | 2.14 | 2.94 | 3.96 | 8.12 | 8.12 | 11.23 |
| Z Value | | | 5.76 | 22.68 | 20.40 | 9.70 | 9.70 | 9.70 | 9.70 | 14.90 | 14.90 |

| (Mass %) | | | Example | | | | Reference Example | |
|---|---|---|---|---|---|---|---|---|
| | | | 10 | 11 | 12 | 13 | 1 | 2 |
| Composition of material for heating | (A) | IPMP | 15 | 15 | 15 | 15 | 2 | 2 |
| | (B) | 1,3-BG | 80 | 80 | 80 | 80 | 50 | 50 |
| | | PG | — | — | — | — | — | — |
| | | Gly | — | — | — | — | — | — |
| | (C) | Purified water | 5 | 5 | 5 | 5 | 48 | 48 |
| | (A) Saturation solubility (25° C.) | | 19.7 | 19.7 | 19.7 | 19.7 | 0.8 | 0.8 |
| | (B)/(A) | | 5.3 | 5.3 | 5.3 | 5.3 | 25.0 | 25.0 |
| Heating conditions | Temperature [° C.] | | 80 | 90 | 70 | 60 | 80 | 80 |
| | Time [min] | | 15 | 5 | 120 | 420 | 10 | 30 |
| Composition of dilute solution | (A) | IPMP | 0.10 | 0.10 | 0.10 | 0.10 | 0.10 | 0.10 |
| | (B) | 1,3-BG | 0.53 | 0.53 | 0.53 | 0.53 | 2.50 | 2.50 |
| | | 1,3-PG | — | — | — | — | — | — |
| | | Gly | — | — | — | — | — | — |
| | (C) | Water | 99.4 | 99.4 | 99.4 | 99.4 | 97.4 | 97.4 |
| | (A) Saturation solubility (25° C.) | | <0.04 | <0.04 | <0.04 | <0.04 | <0.04 | <0.04 |
| Evaluation on dissolubility | | | a | a | a | a | a | a |
| X Value | | | 15 | 5 | 120 | 420 | 10 | 30 |
| Y Value | | | 17.18 | 7.45 | 39.64 | 91.46 | 4.74 | 4.74 |
| Z Value | | | 20.40 | 9.70 | 205 | 1462 | 14.90 | 38.70 |

TABLE 1-2

| (Mass %) | | | Comparative Example | | | | | | | | | |
|---|---|---|---|---|---|---|---|---|---|---|---|---|
| | | | 1 | 2 | 3 | 4 | 5 | 6 | 7 | 8 | 9 | 10 |
| Composition of material for heating | (A) | IPMP | 5 | 10 | 5 | 5 | 5 | 10 | 10 | 15 | 15 | 15 |
| | (B) | 1,3-BG | 80 | 80 | 95 | 95 | 95 | 90 | 90 | 80 | 80 | 80 |
| | | PG | — | — | — | — | — | — | — | — | — | — |
| | | Gly | — | — | — | — | — | — | — | — | — | — |
| | (C) | Purified water | 15 | 10 | 0 | 0 | 0 | 0 | 0 | 5 | 5 | 5 |
| | (A) Saturation solubility (25° C.) | | 9.5 | 13.4 | 21.3 | 21.3 | 21.3 | 21.3 | 21.3 | 19.7 | 19.7 | 19.7 |

TABLE 1-2-continued

|  |  | Comparative Example | | | | | | | | | |
|---|---|---|---|---|---|---|---|---|---|---|---|
| (Mass %) |  | 1 | 2 | 3 | 4 | 5 | 6 | 7 | 8 | 9 | 10 |
|  | (B)/(A) | 16.0 | 8.0 | 19.0 | 19.0 | 19.0 | 9.0 | 9.0 | 5.3 | 5.3 | 5.3 |
| Heating | Temperature [° C.] | 60 | 80 | 80 | 80 | 80 | 80 | 80 | 80 | 90 | 70 |
| conditions | Time [min] | 5 | 5 | 5 | 60 | 1440 | 30 | 180 | 5 | 1 | 30 |
| Composition of | (A) IPMP | 0.10 | 0.10 | 0.10 | 0.10 | 0.10 | 0.10 | 0.10 | 0.10 | 0.10 | 0.10 |
| dilute solution | (B) 1,3-BG | 1.60 | 0.80 | 1.90 | 1.90 | 1.90 | 0.90 | 0.90 | 0.53 | 0.53 | 0.53 |
|  | 1,3-PG | — | — | — | — | — | — | — | — | — | — |
|  | Gly | — | — | — | — | — | — | — | — | — | — |
|  | (C) Water | 98.3 | 99.1 | 98.0 | 98.0 | 98.0 | 99.0 | 99.0 | 99.4 | 99.4 | 99.4 |
|  | (A) Saturation solubility (25° C.) | <0.04 | <0.04 | <0.04 | <0.04 | <0.04 | <0.04 | <0.04 | <0.04 | <0.04 | <0.04 |
| Evaluation on dissolubility |  | b | b | b | b | b | b | b | b | b | b |
| X Value |  | 5 | 5 | 5 | 60 | 1440 | 30 | 180 | 5 | 1 | 30 |
| Y Value |  | 21.07 | 11.23 | 2.22 | 2.22 | 2.22 | 8.24 | 8.24 | 17.18 | 7.45 | 39.64 |
| Z Value |  | 9.70 | 9.70 | 9.70 | 83.40 | 13814 | 38.70 | 370.2 | 9.70 | 5.76 | 38.70 |

Dissolution State Index Ys of Solution 1 of Examples 1 to 13, Reference Examples 1 and 2, Comparative Example 1, 2, and 8 to 10 were determined in accordance with the above (Equation 8). Marks for the solutions in which crystals did not deposit and the solutions in which crystals deposited were plotted on a graph wherein heating times when obtaining each Solution 1 and the above Ys correspond to the X-axis and the Y-axis, respectively, thereby deriving the above (Equation 9) representing a boundary Z. For Comparative Examples 3 to 7, in which water was not included, crystal deposition in Solution 2 was observed despite good dissolution states with Y<Z. The results are shown in FIG. 1.

Examples 14 to 17

Solution 2 was obtained by the same operation as in Example 1, except that purified water and ethanol were used as Component (C) aqueous media and added according to the compositions shown in Table 2 and that the heating conditions shown in Table 2 were used. Table 2 shows the compositions and evaluation results of Solution 2.

Comparative Examples 11 and 12

Solution 1 of the isopropyl methylphenol composition was obtained by carrying out the same operation as in Example 1, except for using purified water and ethanol as Component (C) aqueous media and adding according to the compositions shown in Table 2. Solution 1 was stored still at room temperature (25° C.) for 5 minutes and subsequently diluted with water thereby obtaining Solution 2. Table 2 shows the compositions and evaluation results of Solution 2.

TABLE 2

|  |  | Example | | | | Comparative Example | |
|---|---|---|---|---|---|---|---|
| (Mass %) |  | 14 | 15 | 16 | 17 | 11 | 12 |
| Composition of material for heating | (A) IPMP | 15 | 15 | 25 | 25 | 15 | 25 |
|  | (B) 1,3-BG | 50 | 50 | 50 | 50 | 50 | 50 |
|  | (C) EtOH | 20 | 20 | 20 | 20 | 20 | 20 |
|  | Purified water | 15 | 15 | 5 | 5 | 15 | 5 |
|  | (A) Saturation solubility (25° C.) | 18.4 | 18.4 | 28.7 | 28.7 | 18.4 | 28.7 |
|  | (B)/(A) | 3.3 | 3.3 | 2.0 | 2.0 | 3.3 | 2.0 |
| Heating conditions | Temperature [° C.] | 80 | 60 | 80 | 80 | 60 | 80 |
|  | Time [min] | 1 | 15 | 5 | 15 | 5 | 1 |
| Composition of dilute solution | (A) IPMP | 0.10 | 0.10 | 0.10 | 0.10 | 0.10 | 0.10 |
|  | (B) 1,3-BG | 0.33 | 0.33 | 0.20 | 0.20 | 0.33 | 0.20 |
|  | (C) EtOH | 0.13 | 0.13 | 0.08 | 0.08 | 0.13 | 0.08 |
|  | Water | 99.4 | 99.4 | 99.6 | 99.6 | 99.4 | 99.6 |
|  | (A) Saturation solubility (25° C.) | <0.04 | <0.04 | <0.04 | <0.04 | <0.04 | <0.04 |
| Evaluation on dissolubility |  | a | a | a | a | b | b |
| X Value |  | 1 | 15 | 5 | 15 | 5 | 1 |
| Y Value |  | 11.59 | 46.54 | 20.64 | 20.64 | 46.54 | 20.64 |
| Z Value |  | 19.70 | 85.73 | 38.53 | 85.73 | 38.53 | 19.70 |

Examples 18 to 25

Solution 2 was obtained by the same operation as in Example 1 except that those shown in Table 3 were used as the polyol of Component (B) and added according to the compositions shown in Table 3 and that the heating conditions shown in Table 3 were used. Table 3 shows the compositions and evaluation results of Solution 2.

Comparative Examples 13 to 16

Solution 1 of the isopropyl methylphenol composition was obtained by carrying out the same operation as Example 1, except for using those shown in Table 3 as the polyol of Component (B) and adding according to the compositions shown in Table 3. Solution 1 was stored still at room temperature (25° C.) for 5 minutes and subsequently diluted with water thereby obtaining Solution 2. Table 3 shows the compositions and evaluation results of Solution 2.

TABLE 3

| | (Mass %) | | Example 18 | 19 | 20 | 21 | 22 | 23 | 24 | 25 | Comparative Example 13 | 14 | 15 | 16 |
|---|---|---|---|---|---|---|---|---|---|---|---|---|---|---|
| Composition of material for heating | (A) | IPMP | 5 | 5 | 10 | 10 | 10 | 10 | 3 | 3 | 10 | 10 | 5 | 5 |
| | (B) | 1,3-BG | — | 60 | — | — | 40 | 40 | 60 | 60 | — | — | 60 | 60 |
| | | PG | 85 | — | 80 | — | 40 | — | — | — | — | — | — | — |
| | | Gly | — | 24 | — | 80 | — | 40 | 20 | 20 | — | — | 20 | 20 |
| | | PEG400 | — | — | — | — | — | — | — | — | 80 | — | — | — |
| | | DPG | — | — | — | — | — | — | — | — | — | 80 | — | — |
| | (C) | Purified water | 10 | 11 | 10 | 10 | 10 | 10 | 17 | 17 | 10 | 10 | 15 | 15 |
| | (A) Saturation solubility (25° C.) | | 5.7 | 6.2 | 34.3 | 30.2 | 28.4 | 24.2 | 6.0 | 6.0 | 34.3 | 30.2 | 6.0 | 6.0 |
| | (B)/(A) | | 17.0 | 16.8 | 8.0 | 8.0 | 8.0 | 8.0 | 26.7 | 26.7 | 8.0 | 8.0 | 16.0 | 16.0 |
| Heating conditions | Temperature [° C.] | | 80 | 80 | 80 | 80 | 80 | 80 | 80 | 60 | 80 | 80 | 60 | 70 |
| | Time [min] | | 30 | 15 | 20 | 10 | 10 | 10 | 1 | 20 | 5 | 1 | 20 | 20 |
| Composition of dilute solution | (A) | IPMP | 0.10 | 0.10 | 0.10 | 0.10 | 0.10 | 0.10 | 0.10 | 0.10 | 0.10 | 0.10 | 0.10 | 0.10 |
| | (B) | 1,3-BG | — | 1.20 | — | — | 0.40 | 0.40 | 2.00 | 2.00 | — | — | 1.20 | 1.20 |
| | | PG | 1.70 | — | 0.80 | — | 0.40 | — | — | — | — | — | — | — |
| | | Gly | — | 0.48 | — | 0.80 | — | 0.40 | 0.67 | 0.67 | — | — | 0.4 | 0.4 |
| | | PEG400 | — | — | — | — | — | — | — | — | 0.80 | — | — | — |
| | | DPG | — | — | — | — | — | — | — | — | — | 0.80 | — | — |
| | (C) | Water | 98.2 | 98.2 | 99.1 | 99.1 | 99.1 | 99.1 | 97.2 | 97.2 | 99.1 | 99.1 | 98.3 | 98.3 |
| | (A) Saturation solubility (25° C.) | | <0.04 | <0.04 | <0.04 | <0.04 | <0.04 | <0.04 | <0.04 | <0.04 | <0.04 | <0.04 | <0.04 | <0.04 |
| Evaluation on dissolubility | | | a | a | a | a | a | a | a | a | b | b | b | b |
| X Value | | | 30 | 15 | 20 | 10 | 10 | 10 | 1 | 20 | 5 | 1 | 20 | 20 |
| Y Value | | | 7.13 | 6.45 | 4.39 | 4.98 | 5.30 | 6.22 | 2.26 | 12.01 | 4.39 | 4.98 | 33.37 | 14.46 |
| Z Value | | | 25.20 | 10.13 | 14.30 | 6.80 | 6.80 | 6.80 | 2.96 | 14.30 | 4.33 | 2.96 | 14.30 | 14.30 |

Examples 26 to 29

Solution 2 was obtained by the same operation as Example 1, except that 1,3-butanediol and glycerin were used as the polyol of Component (B) and purified water and ethanol were used as Component (C), each of which was added according to the compositions shown in Table 4 and that the heating conditions shown in Table 4 were used. Table 4 shows the compositions and evaluation results of Solution 2.

Comparative Examples 17 and 18

Solution 1 of the isopropyl methylphenol composition was obtained by carrying out the same operation as Example 1, except that 1,3-butanediol and glycerin were used as the polyol of Component. (B), and purified water and ethanol were used as Component (C), each of which was added according to the compositions shewn in Table 4, and that the heating conditions shown in Table 4 were used. Solution 1 was stored still at room temperature (25° C.) for 5 minutes and subsequently diluted with water thereby obtaining Solution 2. Table 4 shows the compositions and evaluation results of Solution 2.

TABLE 4

|  |  |  | Example | | | | Comparative Example | |
| --- | --- | --- | --- | --- | --- | --- | --- | --- |
|  | (Mass %) |  | 26 | 27 | 28 | 29 | 17 | 18 |
| Composition of material for heating | (A) | IPMP | 3 | 8 | 10 | 8 | 8 | 8 |
|  | (B) | 1,3-BG | 50 | 50 | 50 | 50 | 50 | 50 |
|  |  | Gly | 10 | 10 | 10 | 10 | 10 | 10 |
|  | (C) | EtOH | 15 | 15 | 15 | 10 | 15 | 10 |
|  |  | Purified water | 22 | 17 | 15 | 22 | 17 | 22 |
|  | (A) Saturation solubility (25° C.) | | 14.70 | 14.70 | 15.00 | 8.57 | 14.70 | 8.57 |
|  | (B)/(A) | | 20.0 | 7.5 | 6.0 | 7.5 | 7.5 | 7.5 |
| Heating conditions | Temperature [° C.] | | 80 | 80 | 80 | 50 | 80 | 50 |
|  | Time [min] | | 1 | 5 | 20 | 20 | 1 | 10 |
| Composition of dilute solution | (A) | IPMP | 0.10 | 0.10 | 0.10 | 0.10 | 0.10 | 0.10 |
|  | (B) | 1,3-BG | 1.67 | 0.63 | 0.50 | 0.63 | 0.63 | 0.63 |
|  |  | Gly | 0.33 | 0.13 | 0.10 | 0.13 | 0.13 | 0.13 |
|  | (C) | EtOH | 0.13 | 0.13 | 0.08 | 0.08 | 0.13 | 0.08 |
|  |  | Water | 0.13 | 0.13 | 0.13 | 0.13 | 0.13 | 0.13 |
|  | (A) Saturation solubility (25° C.) | | <0.04 | <0.04 | <0.04 | <0.04 | <0.04 | <0.04 |
| Evaluation on dissolubility | | | a | a | a | a | b | b |
| X Value | | | 1 | 5 | 20 | 20 | 1 | 10 |
| Y Value | | | 0.68 | 4.81 | 7.37 | 76.48 | 4.81 | 76.48 |
| Z Value | | | 4.27 | 26.39 | 189.14 | 189.14 | 4.27 | 66.64 |

Example 30

Methyl p-hydroxybenzoate and 1,3-butanediol were added to purified water respectively to 100 g/L and 800 g/L, thereby obtaining slurries. The obtained slurries were fed into a stainless steel batch reactor having an inner volume of 190 mL (manufactured by Nitto Koatsu Co.) to carry out heating. After the temperature reached 80° C., the temperature was maintained for 1 minute and cooling was carried out (cooling rate 0.3° C./s) to room temperature (25° C.) by immediately immersing the reactor in an ice bath. The immediately cooled solution was taken out, and filtered using a PTFE filter having a pore size of 0.2 μm thereby obtaining Solution 1 of the methyl p-hydroxybenzoate composition. Solution 1 was stored still at room temperature (25° C.) for 60 minutes and subsequently diluted with water thereby obtaining Solution 2.

Table 5 shows the compositions and evaluation results of Solution 2.

TABLE 5

|  | (Mass %) | | Example 30 |
| --- | --- | --- | --- |
| Composition of material for heating | (A) | MP | 10 |
|  | (B) | 1,3-BG | 80 |
|  | (C) | Purified water | 10 |
|  | (A) Saturation solubility (25° C.) | | 17.0 |
|  | (B)/(A) | | 8.0 |
| Heating conditions | Temperature [° C.] | | 80 |
|  | Time [min] | | 1 |
| Composition of dilute solution | (A) | MP | 0.50 |
|  | (B) | 1,3-BG | 4.00 |
|  | (C) | Water | 95.5 |
|  | (A) Saturation solubility (25° C.) | | 0.27 |
| Evaluation on dissolubility | | | a |
| X Value | | | 1 |
| Y Value | | | 8.85 |
| Z Value | | | — |

As is evident from Tables 1 to 5, Solutions 3 of the isopropyl methylphenol composition obtained in Example 1 to 29 and the methyl p-hydroxybenzoate composition obtained in Example 30 did not generate precipitates but maintained a stably dissolved state even when diluted with water to obtain Solution 2 so as to have a concentration above the saturation solubility. Further, when Solutions 2 were stored at room temperature for 1 month, stably dissolved state was maintained.

In Examples 1 to 29, in which Solutions 1 were prepared so as to contain isopropyl methylphenol in a concentration below the saturation solubility (25° C.), it was confirmed that stability in a dissolved state of the (A) hardly water-soluble aromatic compound in Solution 1 is higher after it was cooled to room temperature (25° C.) via the heating, compared to Reference Examples 1 and 2, in which Solutions 1 were prepared so as to contain isopropyl methylphenol in a concentration above the saturation solubility (25° C.).

The invention claimed is:

1. A method for producing a composition containing a hardly water-soluble aromatic compound, comprising:
   Step (1) of obtaining a hardly water-soluble aromatic compound solution 1, Step (1) comprising Step (1-1) of preparing a material for heating comprising (A) a hardly water-soluble aromatic compound, (B) a polyol, (C) an aqueous medium and optionally (D) a surfactant, and Step (1-2) of obtaining a heated solution containing the hardly water-soluble aromatic compound by heating the material for heating without applying a pressure at a temperature of 50° C. or more and less than 100° C.; and
   Step (2) of obtaining a hardly water-soluble aromatic compound solution 2 by adding water to the hardly water-soluble aromatic compound solution 1 after the material for heating is cooled to 0 to 35° C. such that the hardly water-soluble aromatic compound solution 2 has a concentration of the (A) hardly water-soluble aromatic compound above a saturation solubility at 25° C.,
   wherein, in Step (1), a content of the (D) surfactant in the material for heating is 0.1 mass % or less and a content of the (A) hardly water-soluble aromatic compound in the material for heating is below a saturation solubility of the (A) hardly water-soluble aromatic compound in a solvent composed of (B) the polyol and (C) the aqueous medium, having the same composition at 25° C., wherein, in Step (1-1), a mass ratio of the (B) polyol to a total mass of the (B) polyol and the (C) aqueous medium, (B)/[(B)+(C)], in the material for heating is from 0.45 to 0.98, and wherein the (A) hardly water-soluble aromatic compound is at least one of triclosan, chlorothymol, carvacrol, chlorophen, dichlorophen, hexachlorophene, chloroxylenol, chlorocresol, methyl parahydroxybenzoate (=methyl paraben), ethyl parahydroxybenzoate (=ethyl paraben), propyl parahydroxybenzoate (=propyl paraben), isopropyl parahydroxybenzoate (=isopropyl paraben), butyl parahydroxybenzoate (=butyl paraben), isobutyl parahydroxybenzoate (=isobutyl paraben), and benzyl parahydroxybenzoate (=benzyl paraben); and o-phenylphenol, and isopropyl methylphenol.

2. The method according to claim 1, wherein, in Step (1-1), a mass ratio of the (B) polyol to the (A) hardly water-soluble aromatic compound, (B)/(A), in the material for heating is 1 or more and 80 or less.

3. The method according to claim 1, wherein the (A) hardly water-soluble aromatic compound is an aromatic compound having solubility of 3.0 g/L or less in water at 25° C.

4. The method according to claim 1, wherein the (A) hardly water-soluble aromatic compound is an aromatic compound having solubility of 5 g/L or more in polyol at 25° C.

5. The method according to claim 1, wherein the (A) hardly water-soluble aromatic compound is one or more selected from the group consisting of isopropyl methylphenols and para-hydroxybenzoates.

6. The method according to claim 1, wherein the (B) polyol is one or more selected from the group consisting of a dihydric alcohol, a trihydric alcohol, and a condensate thereof.

7. The method according to claim 1, wherein the (C) aqueous medium is water or an aqueous solution of a monohydric alcohol.

8. The method according to claim 1, wherein heating time in Step (1-2) is 6 minutes or more and 120 hours or less.

9. The method according to claim 1, wherein the Component (B) is 1,3-butanediol and the Component (C) is water in Step (1-1), and the material for heating is heated in Step (1-2) under a condition that a relation between Dissolution State Index Y represented by the following (Equation 8) and heating time t satisfies the following (Equation 9):

$$\text{Dissolution Index } Y = \frac{C_0^2}{C_s} \times E = \quad \text{(Equation 8)}$$

$$\frac{C_0^2}{C_s} \times [17.4 e^{0.085 C_{BG}} e^{\{-0.046T\}}] e^{\{-0.00047 T C_{BG} - 0.032 C_{BG}\}}$$

$$Y < 0.006t^2 + 0.95t + 4.8 \quad \text{(Equation 9)}$$

wherein $C_0$ represents a concentration of Component (A), $C_s$ represents a saturation solubility of Component (A), E represents the Dissolution Efficiency, $C_{BG}$ represents a concentration of Component (B) in Component (B)+Component (C), T and t represent a heating temperature and heating time, respectively, in Step (1-2).

10. A method for producing a cosmetic product, comprising a step of adding the composition containing the hardly water-soluble aromatic compound, obtained by the method of claim 1.

* * * * *